United States Patent [19]

Dunger et al.

[11] Patent Number: 5,466,670
[45] Date of Patent: Nov. 14, 1995

[54] USE OF IGF-1

[75] Inventors: David B. Dunger, Oxford; Martin O. Savage; Peter H. Sönksen, both of London, all of Great Britain

[73] Assignee: PHARMACIA AB, Sweden

[21] Appl. No.: 175,404

[22] PCT Filed: May 14, 1993

[86] PCT No.: PCT/SE93/00425

§ 371 Date: Feb. 1, 1994

§ 102(e) Date: Feb. 1, 1994

[87] PCT Pub. No.: WO93/23071

PCT Pub. Date: Nov. 25, 1993

[30] Foreign Application Priority Data

May 19, 1992 [SE] Sweden ................................. 9201573

[51] Int. Cl.⁶ ......................... A61K 38/05; A61K 38/06; C07K 5/00
[52] U.S. Cl. .................................................. 514/12
[58] Field of Search ................................. 514/12

[56] References Cited

FOREIGN PATENT DOCUMENTS

| | | |
|---|---|---|
| 0123228A2 | 10/1984 | European Pat. Off. . |
| 0308386A1 | 3/1989 | European Pat. Off. . |
| 0331630A1 | 9/1989 | European Pat. Off. . |
| 218811 | 7/1991 | New Zealand . |
| WO91/03253 | 3/1991 | WIPO . |

OTHER PUBLICATIONS

Diabetologia, vol. 34, 1991, E. J. Schoenle, et al., "Recombinant human insulin–like growth factor I (rhIGF I) reduced hyperglycaemia in patients with extreme insulin resistance" pp. 675–679.
Trends in Endocrinology and Metabolism, Volume, May 1990 (6), E. Rudolf Froesch, et al., "Therapeutic Potential of Insulinlike Growth Factor I" pp. 254–260.
Diabetes, vol. 40, Apr. 1991, Luciano Rossetti, et al., "Metabolic Effects of IGF–I in Diabetic Rats" pp. 444–448.
Chemical Abstracts, vol. 114, No. 114, 15 Apr. 1991 (15.Apr.1991), (Columbus, Ohio, USA), Jacob, Ralph J., et al., "Metabolic effects of IGF–I and insulin in spontaneously diabetic BB/w rats" p. 109, The Abstract No. 136379k.
Amiel, S. A. et al., (1986) N. Engl. J. Med. 315, 215–219, Impaired insulin action in puberty.
Guler, H. P. et al. (1987) N. Engl. J. Med. 317, 137–140 Short term metabolic effects of recombinant human insulin.

*Primary Examiner*—Jill Warden
*Assistant Examiner*—Benet Prickril
*Attorney, Agent, or Firm*—Pollock, Vande Sande & Priddy

[57] ABSTRACT

The invention relates to the use of IGF-1 for the manufacture of a medicament for treatment of Type 1 diabetes mellitus. the medicament comprising a subcutaneous dose not greater than needed to achieve an IGF-1 serum level characteristic for healthy individuals i.e. a physiological replacement of serum IGF-1. This treatment would be especially valuable for the treatment of children or adolescents with Type 1 diabetes mellitus and could lead to improvements in their pubertal growth.

13 Claims, 6 Drawing Sheets

USE OF IGF-1

The present invention relates to the use of insulin-like growth factor (IGF-I) for the manufacture of a medicament for treatment of Type 1 diabetes mellitus (IDDM), the medicament comprising a subcutaneous dose to achieve an IGF-I serum level characteristic for healthy individuals, especially in children, adolescents and young adults. Evidence for the efficacy of such treatment is presented in adolescents with insulin dependent Type 1 diabetes mellitus.

BACKGROUND

Human IGF-I (hIGF-I) is a peptide present in plasma and other body fluids. It has been purified from human plasma and the complete amino acid sequence is known. The primary sequence comprises 70 amino acids, including 3 disulphide bonds. Moreover, purified IGF-I:s from plasma of other species show extensive sequence homologies to hIGF-I.

hIGF-I can stimulate growth of a wide range of cell types. It has both systemic and local effects and is present in the circulation mainly associated with different binding proteins, six of which are sequenced (IGFBP1-6). The binding proteins appear to modulate the biological functions and availability of IGF-I variably. IGF-I analogues with changed biological activities seemingly related to changes of affinities to the binding proteins have been produced. IGF-I appears to act mainly through the IGF-type 1 receptor exposed on the outer surface of many different cell types. However, the relative specificity of action may vary at the cell level, for example, due to varying influence of binding proteins. The structures of the IGF-I and insulin receptors are closely homologous, but binding of IGF-I and insulin show only limited cross-reactivity.

Because of the scarcity of purified plasma hIGF-I, there was a great need to develop methodology for a commercial scale production. Nowadays such large scale production of hIGF-I can readily be achieved by using recombinant DNA techniques.

IGF-I is primarily involved in mediating the somatogenic effects of growth hormone (GH). As a result of studies with preparations of recombinant DNA derived hIGF-I, it has been demonstrated that it promotes skeletal growth and skeletal muscle protein synthesis. Moreover, hIGF-I is also effective for the treatment or prevention of catabolic states (WO 92/03154)).

In WO 91/12018 (Ballard et al.) the therapeutic use of IGF-I, or a peptide analogue thereof, for gastrointestinal disease or the treatment of the shortened gut after surgery was disclosed.

It has also been found that IGF-I improves the regeneration of transected periferal nerves (EP 308 386) and it has previously been demonstrated in vitro that IGF-I promotes actin synthesis in myocytes in culture (Florini, J. R., Muscle and Nerve, 10 (1987) 577–598), and contractility of neonatal rat cardiocytes (Vetter, U. et al., Basic Res. Cardiol. 83 (1988) 647–654.

Large doses of hIGF-I do lower blood glucose in non-diabetic animals and humans (Zapf J. et al. J Clin-Invest, Jun Vol:77(6) (1986) 1768–75 and Guler H-P et al, N Engl. J. Med, 317 (1987) 137–140). In these studies the hypoglycaemic effect of hIGF-I was around 1.5–7% of that of insulin. Recent studies in the depancreatised dog demonstrated that as an agent for lowering blood glucose hIGF-I was 8–11% as potent as insulin (Giacca A. et al., Diabetes, 39 (1990) 340–347). However, these studies also demonstrated that the metabolic effects of IGF-I may be quite distinct from those of insulin. The glucose lowering effects of IGF-I were largely mediated by increased glucose uptake, while glucose production rates remained unchanged. One explanation for this observation might be the relative paucity of IGF-I receptors in adult liver (Caro J. F. et al., J. Clin. Invest, 81 (1988) 976–981). It is likely that the effects of IGF-I are largely mediated through muscle. Similar distinctions in the distribution of receptors may explain the less potent antilipolytic effects of IGF-I as compared to insulin in vitro (Bolinder et al, J. Clin. Endocrinol. Metab, 65, (1987) 732–737) and in vivo (Zapf J. et al. 1986, Guler H-P et al. 1987, Giacca A et al. 1990). IGF-I decreases proteolysis and reduces amino acid levels in non-diabetic rats (Jacob R. et al., J Clin. Invest, 83, (1989) 1717–1723). Furthermore, in the studies of Giacca A. et al. ,1990, a rise in lactate was observed which did not occur with an equipotent dose (for glucose lowering) of insulin.

IGF-I circulates predominantly as a large 150K complex (IGFBP3) comprising a 53K GH-dependent acid stable IGF binding component and an acid labile subunit. The smaller 28–35K binding protein (IGFBP1) is not growth hormone dependent and shows a marked circadian variation which is inversely related to insulin (Brismar K. et al., J Endocrinol Invest, 11(1988) 599–602, Cotterill A. M. et al, J Clin Endocrinol Metabol, 67 (1988) 882–887, Holly J. M. P. et al., Clin Endocrinol, 29 (1988) 667–675). Measured circulating IGF-I level appears to be mainly determined by the available capacity of IGFBP3 whereas IGFBP1 seems to be primarily involved in other functions such as transport of IGF-I from the circulating pool or modulation of biological actions in the tissues (Holly J. M. P. et al., J Endocrinol, 121 (1989) 383–387, and Diabetic Medicine, 7 (1990) 618–23).

Insulin deficiency also results in high levels of IGFBP1 which is believed to inhibit the biological activity of IGF-I (Taylor A. M. et al., Clin Endocrinol, 32 (1990) 229–239).

Age-related changes in plasma IGF-I in healthy subjects have been investigated (Smith C. P. et al, J Clin. Endocrin. Metab, Vol 68, No 5, (1989) 932–937). It was found that basal plasma IGF-I concentrations rose significantly throughout puberty and declined to prepubertal levels by the third decade of life. The concentration was about 1 U/ml before and after puberty and about 2 U/ml during puberty.

It was not previously known how the different IGFBP profile in diabetics would affect the bioavailibility or bioactivity of endogenous or exogenously administered IGF-I.

Increased overnight GH serum concentrations have been compared between diabetic and normal adolescents (Edge J. A. et al, J. Clin. Endocrinol. metab, Vol. 71, No 5, (1990) 1356–1362) and it was found that GH baseline and peak levels were higher in the diabetic than in the control subjects.

In EP 331 630 (Ciba-Geigy) a method is disclosed for treatment and preventing secondary effects of hyperinsulinaemia in Type 1 diabetes mellitus by administrating hIGF-I. In the description the dose of hIGF-I used is around 500 µg/kg/day. hIGF-I was given to two healthy (non-diabetic) subjects receiving 20 µg/kg/h during six days by continuous subcutaneous infusion. The amount given per day is 10 times the endogenous production of hIGF-I (approximately 50 µg/kg/day). With such a high dose of hIGF-I an insulin-like effect is to be expected.

The authors interpreted the results obtained as indicating that these high doses of IGF-I resulted in a decrease of insulin degradation and a prolongation of its half-life. They concluded that hIGF-I makes the organism more sensitive to insulin and therefore a lower dose of insulin can be used. Thus, by administration of hIGF-I, less exogenous insulin would be needed and hyperinsulinaemia due to large doses of insulin can be avoided or minimised. However, the route of administration and particularly the high doses used in the example have a very limited clinical applicability. The dose 480 μg/kg/day given as a continuous infusion results in very high (supraphysiological) serum levels of IGF-I. Such concentrations cannot be regarded as safe and clinically applicable.

In contrast to the findings in EP 331 630, we have found that a physiological restoration of circulating IGF-1 levels gives reduced GH levels through a feed back mechanism. This normalisation of GH and IGF-I levels lead to an increased sensivity for insulin and to a reduction in the dawn phenomenon (the rapid increase in the morning blood glucose levels seen in type 1 diabetics) and thereby providing better long term control.

The possible clinical value of a therapy with IGF-I to restore physiological IGF-I levels and thereby alter the growth hormone/IGF-I axis, have not earlier been considered.

The GH/IGF-I axis in diabetes

Insulin dependent diabetes causes profound derangements in the GH/IGF-I axis. In poorly controlled Type 1 diabetics, GH levels are invariably raised. The elevated GH levels are characterised by a greater pulse amplitude and higher baseline concentration of GH as compared to the levels of normal subjects. Recent studies on the signal mode of GH indicate that it is the pulse amplitude rather than the increased baseline which lead to profound changes in insulin resistance in diabetic subjects (Pal et al., Diabetologia, in press). The high GH levels lead to insulin resistance and aggravate the metabolic abnormalities of diabetes. GH excess has also been implicated in the aetiology of the dawn phenomenon and may accelerate the development of microangiopathy including proliferative retinopathy. Finally, an excessive rise in beta hydroxy buturate (BOH) caused by raised GH has been observed, particularly during puberty, and is compounded by the effects of insulin waning overnight; this leads to the risk of rapid decompensation with diabetic ketoacidosis in adolescents with diabetes.

Despite the elevated GH levels, IGF-I levels tend to be low in diabetes and this is related to decreased GH receptor function resulting from low levels of insulin (Holly J. M. P. et al., Clin. Endocrinol, 29 (1988) 667–675). The lower IGF-I levels in the presence of elevated GH levels has been implicated in the slow growth and loss of adult height in children with diabetes (Salardi S. et al. Arch. Dis. Child, 62, (1987) 57–62).

The mechanism underlying the increased GH levels has been the subject of some controversy. In the diabetic individual hyperglycaemia does not inhibit GH secretion as it does in healthy individuals and it has been proposed that this reflects an altered hypothalamic function. This altered hypothalamic function is characterised by reduced somatostatin levels and resistance to the effects of somatostatin. Suppression of plasma GH by somatostatin analogues and pirenzepine has led to reported improvement in metabolic control. However, this approach has proved inappropriate during childhood and adolescence when growth is rapid as it would inevitably lead to growth failure.

It has been argued that the excessive GH release may relate to low IGF-I levels. However, Shaper et al. (Acta Endocrinol, 122 (1990), suppl, 32–39) reasoned against this hypothesis as they could not observe any negative correlation between serum IGF-I levels and GH responses to GH releasing hormone in such patients.

In light of this controversy it is remarkable that our preliminary studies indicated that a single subcutaneous physiological replacement dose of IGF-I in adolescents with diabetes led not only to a reduction in GH levels but also to a statistically significant reduction of insulin requirement on that single occasion. The relatively long-lasting effect from a single injection was also surprising and opens the possibility of single dose subcutaneous administration, especially in treatment of children, adolescents and young adults with diabetes.

THE INVENTION

Figure 1A:
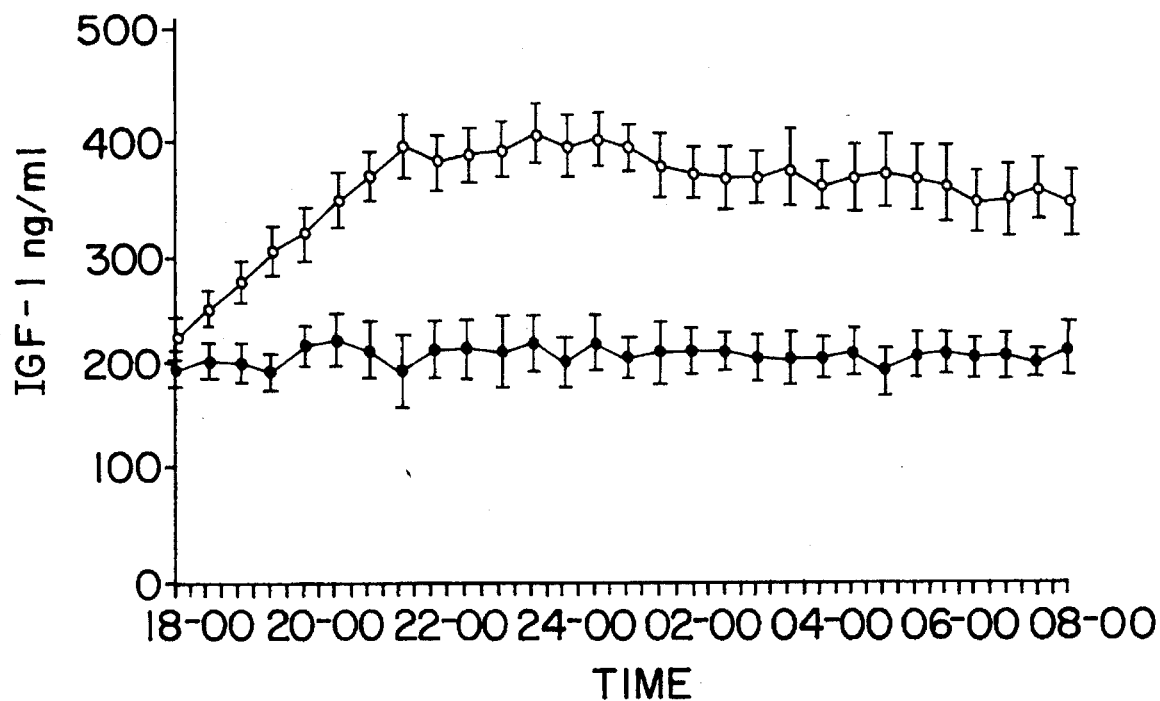
FIG. 1: Mean blood glucose and mean IGF-I levels at 18.00 to 09.00 hours

Our study is the first study in diabetics which shows that IGF-I given in physiological doses has a significant feedback effect on GH levels and GH secretion. Physiological replacement of IGF-I led to a significant reduction of insulin requirement which was mediated by the reduction in GH levels rather than any direct effects of free IGF-I as reported in previous studies.

The invention relates to the use of IGF-I for the manufacture of a medicament for treatment of Type 1 diabetes mellitus, (IDDM, Insulin Dependant Diabetes Mellitus) the medicament comprising a subcutaneous dose to achieve an IGF-I serum level characteristic for healthy individuals i.e. not greater than needed to achieve the physiological replacement of IGF-I in serum. This treatment would be especially valuable for the treatment of children, adolescents or young adults with Type 1 diabetes mellitus and could lead to improvements in their pubertal growth.

The medicament can also be used for an improved and stabilised glycaemic control, for reduced brittleness, for reduced risk for acute decompensation and for reduced incidence of diabetic Ketoacidosis in Type 1 diabetes mellitus.

The invention also relates to the use of IGF-I for the manufacture of medicament comprising a subcutaneous dose to achieve an IGF-I serum level characteristic for healthy individuals for reducing insulin requirements for children, adolescents and young adults with Type 1 diabetes mellitus.

The medicament cold comprise IGF-I alone or be in combination with an insulin preparation.

The medicament is preferably adapted for a single injection which could be given once or twice a day, one, two or three times a week or from one up to seven days per month. The medicament can also be given as a depot or slow release preparation and should thereby be adopted for that. The invention also relates to a method for the treatment of Type 1 diabetes mellitus, the medicament comprising a subcutaneous dose to achieve an IGF-I serum level characteristic for healthy individuals.

The physiological serum IGF-I level is about 1 U/ml for a healthy adult and about twice as high during puberty. 1 U/ml of IGF-I corresponds to about 200 ng/ml of IGF-I.

The invention is novel and inventive because it was never previously realised that the restoration of normal IGF-I bioactivity would lead to such dramatic reductions in GH secretion and profound effects on insulin requirement. The implications for this invention are profound in that IGF-I treatment might lead to prolonged improvements in glycaemic control and a reduction in the risk of diabetic complications.

This discovery was surprising in that the previous studies indicated that, in normal subjects, only pharmacological doses of IGF-I would lead to any GH suppression. Further, it was argued that IGF-I would only be of value in diabetics if used in the pharmacological doses necessary to obtain direct insulin-like effects. The profound effects of physiological replacement therapy in Type 1 diabetes mellitus has never previously been proposed.

The clinical improvements would include:

Improved glycaemic control and consequences thereof (e.g. normalisation of serum lipids, reduced risk for late vascular complications)

Stabilised glycaemic control, e.g. reduced brittleness (fewer unpredictable and incapacitating episodes of hyper- and hypoglycaemia) and reduced risk for acute decompensation Reduced incidence of diabetic ketoacidosis.

A more normalised pubertal growth.

EXAMPLES

Assays

Whole blood glucose, measured every 15 minutes, was determined by the glucose oxidise method (YSI analyser, Clandon Scientific Ltd, Hants, UK).

Samples for GH assay, taken every 15 minutes, were kept at room temperature until the profile was complete and then they were spun, separated and the plasma frozen at −20° C. until assay. Plasma GH concentrations were measured by immunoradiometric assay (IRMA.) using the International Reference Standard 80/505. All the samples from each individual profile were analysed in the same batch. The inter-assay coefficients of variation at GH concentrations of 3.5, 15.2 and 77.4 mU/L were 9.4, 7.7 and 10.5%, respectively, and the nitre-assay coefficients of variation at GH concentrations of 2.9, 14.3 and 69.4 mU/L were 8.0, 2.0 and 3.4%, respectively.

For plasma free insulin, measured hourly, 1.0 ml of whole blood was added immediately to 0.6 ml of ice-cold 25% polyethylene glycol (PEG 6,000) and then spun at 300 rpm for 20 minutes before separation (Collins A. C. G. and Pickup J. C., Diab Med, 2 (1985) 456–460). The plasma was stored at −20° C. and assayed by a double-antibody radioimmunoassay (Guildhay Antisera Ltd) modified from Morgan and Lazarow (Diabetes, 12 (1963) 115–126). Interassay coefficients of variation at 12.2 and 47.2 mU/L were 5.5 and 8.6%, respectively.

A pulse detection programme, Pulsar (Merriam G. R. and Wachter K. W., Am J Physiol, 243 (1982) E310-E318) was used to analyse 12 hour GH profiles between 22.00 and 08.00 hours. It detects hormone pulses as deviations from a smoothed detrended baseline using the assay standard deviation as a scale factor.

Blood glucose and insulin infusion data were normally distributed. Log-transformation normalised the plasma free insulin data and therefore parametric statistical techniques were used. Analyses of variance (Two-way ANOVA) was used to examine changes with time. Data are expressed as Mean±Standard Error of the Mean (SE) unless otherwise stated.

Glycosylated haemoglobin ($HbA_{1c}$) was measured by using the Diamat Dedicated HPLC System.

Plasma IGF-I was measured by standard RIA after acid-ethanol extraction. The maximum sensivity of one assay is 10 µg/l. The inter-and intra-assay variations were less than 10% and 8% respectively, at analyte concentration 2 3, 1.2 and 0.2 µg/ml.

Example 1

Nine adolescents with Type 1 Insulin Dependent Diabetes (five females and four males) aged between 14 and 18 years and at late puberty stage 4 or 5 (Tanner) participated in a cross-over double-blind placebo-controlled trial of IGF-I administered subcutaneously at a dose of 40 µg/kg body weight. The volume of IGF-I or placebo subcutaneously administered, calculated at 40 µg/kg body weight, was in the range of 1.0 to 1.5 ml IGF-I or placebo was given at 18.00. Blood glucose was controlled at 5 mmol/L overnight by an insulin varying glucose clamp. When treated according to the Group A protocol the subjects received placebo and when treated in Group B they received IGF-I. The duration of the study was 22 hours.

Subjects were of normal height and weight (median weight 62.5 kg, range 50.3 to 73.9 kg) with a Body Mass Index (BMI) less than 26 $kg/m^2$ and had been diagnosed as having Type 1 diabetes for at least 3 complete years. C-peptide levels ranged from less than 0.025 to 0.275 nmol/L (median 0.047 nmol/L). The subjects were in good general health with normal hepatic, renal and thyroid function and were all using a combination of short and intermediate acting insulin administered either twice or four times daily (median dose 1.0 U/kg/day, range 0.6 to 1.5 U/kg/day). Subjects were not taking any regular medication apart from one individual who inhaled beclomethasone diproprionate, 200 µg three times daily for treatment of asthma. Median glycated haemoglobin (Total HbA1) at the time of the study was 13.5% with a range of 7.1 to 17.0%. Details of the subjects participating in the study are summarised in Table I.

TABLE I

| | PATIENT DETAILS | | | | | | | | |
|---|---|---|---|---|---|---|---|---|---|
| NUMBER | 1 | 2 | 3 | 4 | 5 | 6 | 7 | 8 | 9 |
| AGE (years) | 14 | 14 | 17 | 14 | 18 | 18 | 17 | 15 | 15 |
| SEX | M | F | M | F | F | F | M | F | M |
| PUBERTY STAGE (G/P.H.) | 5/4 | 4/4 | 5/5 | 5/5 | 5/4 | 5/5 | 5/5 | 4/4 | 5/5 |
| WT. (kg) | 61.0 | 50.3 | 64.0 | 66.9 | 51.4 | 73.9 | 72.0 | 54.9 | 68.2 |
| INSULIN DOSE (mU/kg) | 1.0 | 1.5 | 0.8 | 1.0 | 1.3 | 0.6 | 1.5 | 0.9 | 1.2 |
| HbA1 (%) | 17.0 | 15.6 | 7.1 | 15.5 | 14.3 | 10.5 | 13.3 | 13.7 | 8.4 |

One subject (3) was excluded from most of the analysis because of asymptomatic hypoglycaemia during the study, see below. Of the remaining eight patients four had been randomised to receive IGF-I during the first study period.

Results

Blood glucose

No subject experienced hypoglycaemic symptoms during the study period overnight. However, for subject 3 the lowest blood glucose was 3.3 mmol/L during Period A and 2.5 mmol/L during Period B under placebo and IGF-I treatment, respectively. In both instances the individual concerned was subject number 3. For the purposes of this study hypoglycaemia has been defined as values below 3.5 mmol/L. By adopting a relatively high threshold we hope to have ensured that counter-regulatory responses to hypoglycaemia which could affect the study outcome have not been evoked. Data from the two study periods for subject number 3 has therefore been excluded from the overall analysis of growth hormone production and insulin requirements. The two study periods were one or two weeks apart, except in one subject where they were six weeks apart.

Figure 1B:
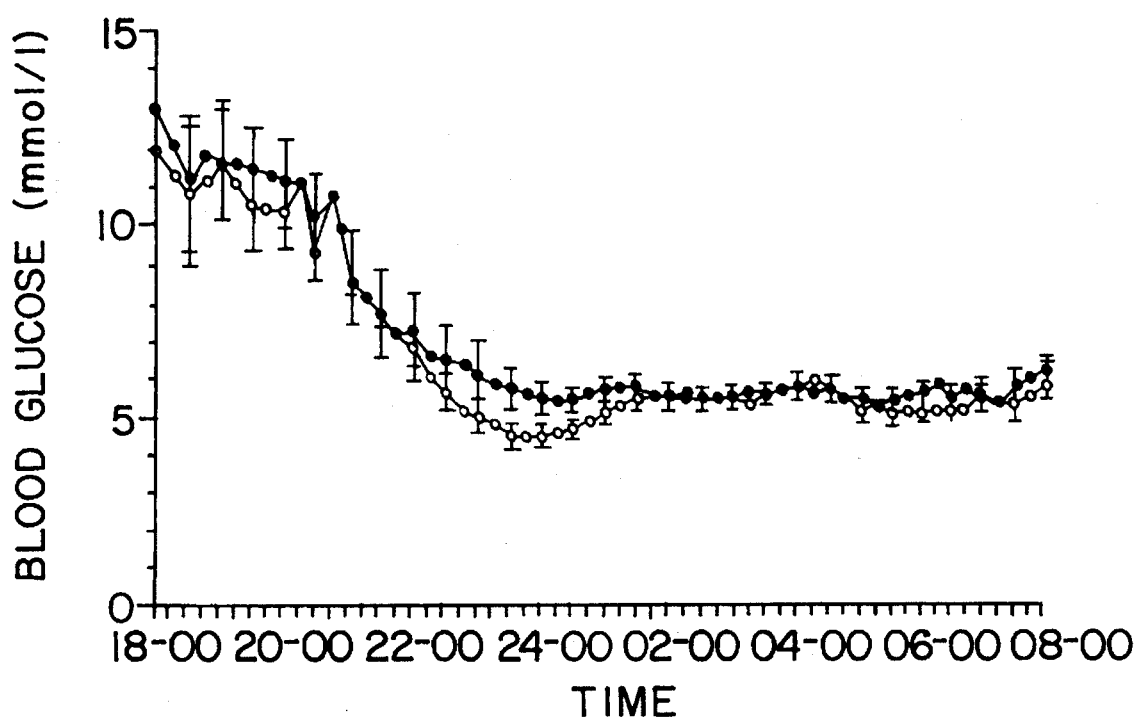

A stable blood glucose was reached by 02.00 hours in both groups of subjects, and remained stable throughout 08.00 hours. See FIG. 1. Mean blood glucose between 02.00 and 08.00 hours in study groups A (control) and B (IGF-I) was 5.62±0.13 and 5.59±0.07 mmol/L, respectively. Two-way analysis of variance between groups and within groups did not reveal any significant difference in blood glucose values.

IGF-I

Mean blood levels of IGF-I rose from 223.2 ng/ml to a peak of 413.1 ng/ml 5.5 hours after the injection of recombinant IGF-I. Levels 30 minutes post-injection were significantly higher than after placebo administration (251.8±17.6 versus 202.1±18.7 ng/ml, p=0.002) and then remained elevated throughout the study period overnight. Overall mean values on IGF-I study night: 359.4±25.9 versus placebo: 206.1±22.3 ng/ml: p<0.001) see FIG. 1.

Growth hormone

Growth hormone production has been analysed throughout the study period (18.00 to 16.00) and also overnight between 20.00 and 08.00. Mean values obtained from 15 minute sampling have been used.

Figure 2:
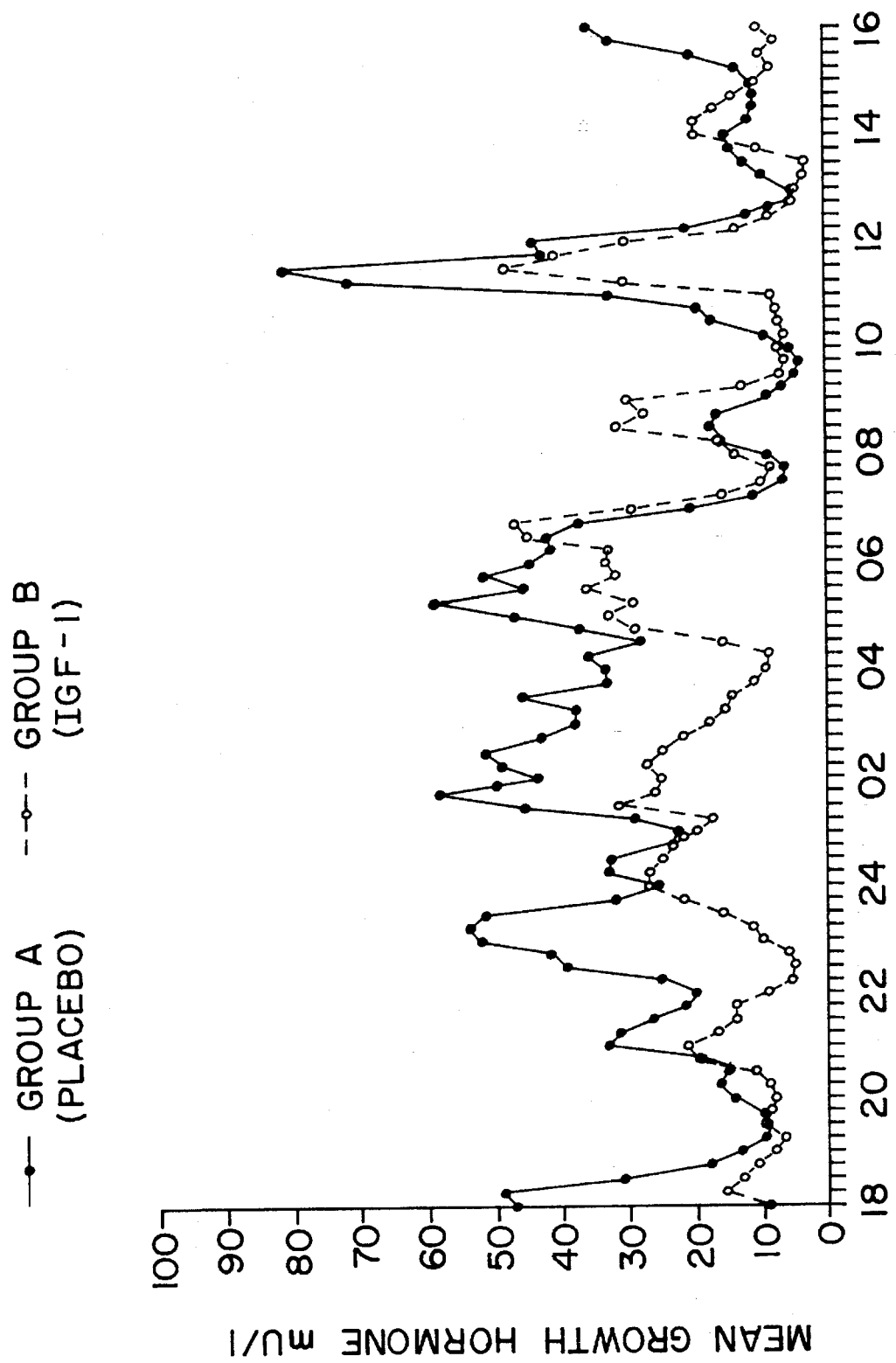
FIG. 2: Mean growth hormone levels at 18.00 to 16.00 hours

There was an overall significant reduction in growth hormone levels in the period when IGF-I was administered when compared to the period when placebo was given (16.92±3.21 versus 27.77±4.88 mU/L; p=0.011 paired "t" test). Mean values throughout the 22 hours are shown in FIG. 2.

Figure 3:
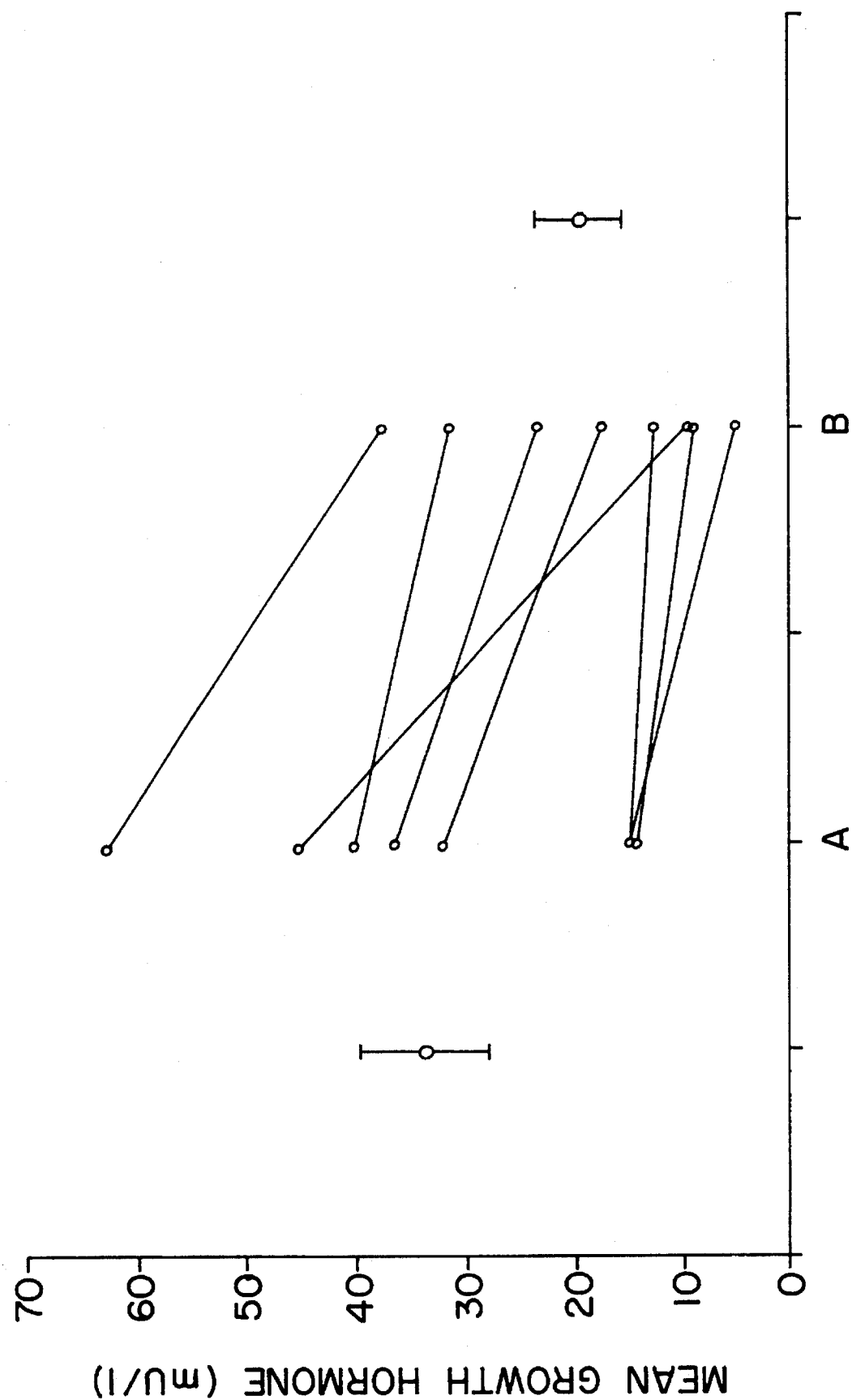
FIG. 3: Mean growth hormone levels for Group A and Group B and per individual at 20.00 to 08.00 hours

A significant reduction was also seen overnight from 20.00 until 08.00 hours (19.38±4.03 versus 33.65±5.78 mU/L; p=0.009; paired "t" test). See FIG. 3.

The Pulsar programme demonstrated a significant reduction in growth hormone mean peak amplitude after IGF-I administration (41.1±7.1 versus 75.2±12.2 mU/L; p=0.01) and in the mean calculated baseline growth hormone concentrations (1.4±0.5 versus 8.2±2.5 mU/L; p=0.02)

Insulin

Insulin requirements during the 22 hours study period can be divided into the initial stage leading to the establishment of a stable blood glucose, the clamp period itself and finally the interval between breakfast and the study ending at 16.00 hours. The insulin infused between the time of IGF-I or placebo administration and the establishment of a stable insulin varying glucose clamp at 02.00 hours was not significantly different between group A (IGF-I) and group B (control); (0.57±0.08 versus 0.51±0.06 mU/kg/min; p=0.436).

Figure 4:
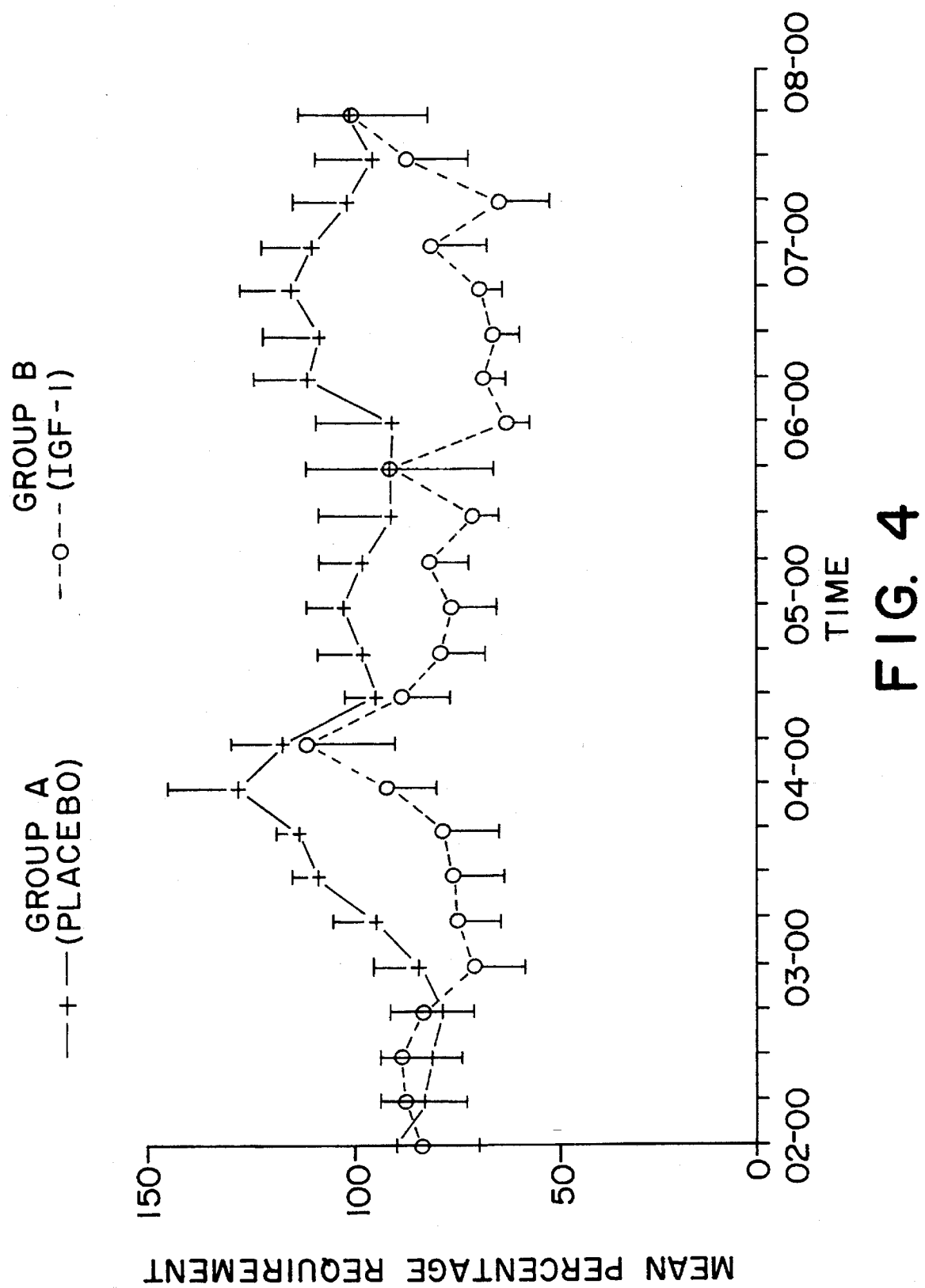
FIG. 4: Mean serum insulin levels at 02.00 to 08.00 hours

A stable blood glucose was established by 02.00 hours as described above. Analysis of the insulin infusion during the period 02.00 to 08.00 hours showed a significant reduction in the insulin requirements to maintain euglycaemia in the group receiving IGF-I when compared to the control group. (0.25±0.12 versus 0.31±0.07 mU/kg/min; p=0.03 paired "t" test). The insulin infusion data (U/kg body weight) has also been analysed by an assessment of percentage change during the period 02.00 to 08.00 hours. By using the mean insulin requirement in Group A treatment in each individual subject as the divisor, the overall difference between Groups A and B during the clamp has been expressed as a mean percentage at each individual time point. See FIG. 4.

Because the insulin requirement for Group A has been used as the divisor the overall sum of the percentage values in that group will be one hundred. Paired "t" testing of the mean percentage values for Groups A and B in each individual subject confirms the significant reduction in insulin requirement after IGF-I administration. (81.4 versus 100%; p=0.002).

Figure 5:
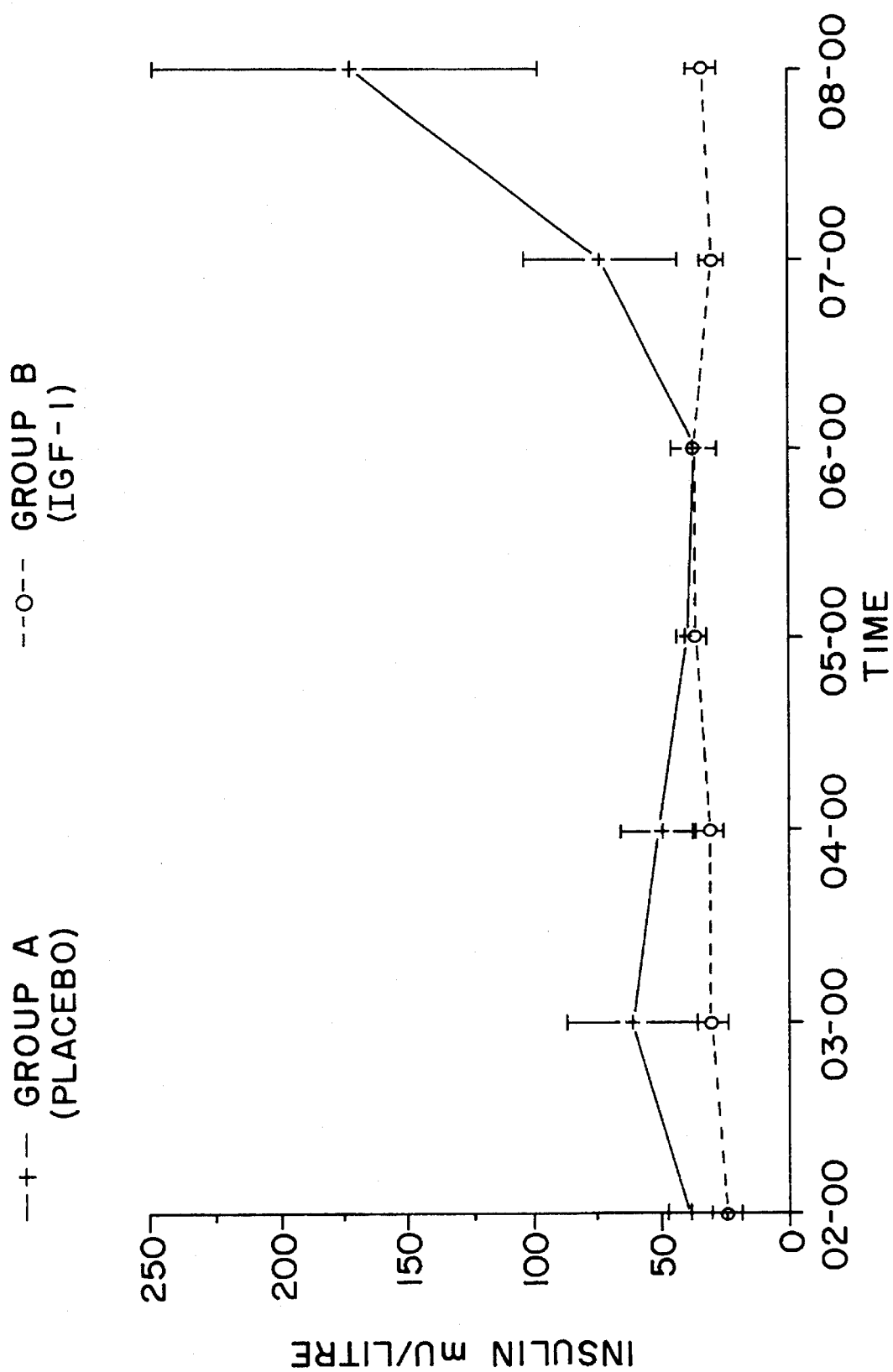
FIG. 5: Mean percentage insulin requirement during stable blood glucose levels at 02.00 to 08.00 hours

Mean plasma free insulin levels were also reduced during this period after IGF-I administration (67.88±15.96 versus 31.90±2.74 mU/L; p=0.001) FIG. 5.

Example 2

A follow up study was undertaken in order to evaluate whether IGF-I levels were sustained over a 28 days treatment period with IGF-I, i.e. that the endogenous production of IGF-I was not suppressed.

Four male patients with type 1 insulin dependent diabetes mellitus aged between 15 and 19 years and of Tanner puberty stages 3–5 for genitalia and 2–5 for pubic hair, respectively, were treated with rhIGF-I during a 4-week period.

| Visit | −4 weeks—1 week: | Screening visits |
|---|---|---|
| Visit | 0 week: | First injection of IGF-I given at 18.00, thereafter overnight profile. |
| Visit | 1 week–4 weeks: | Treatment period, last IGF-I injection given at 18.00 on 4 week visit, thereafter overnight profile. |
| Visit | 8 week: | Follow-up visit |

The dose of 40 μg/kg IGF-I was administered subcutaneously in the thigh once daily at 18.00 hours for 28 consecutive days.

All subjects participating in the study had a diabetes duration of at least 5 years (range 5–10 years). The subjects were in good health with normal hepatic and renal function. All patients were euthyroid at initiation of treatment and were using a combination of short and intermediate acting insulin administered four times daily.

Subjects were not taking any regular medication than insulin. Median glycated haemoglobin A ($HbA_1/HbA_{1c}$) at the screening visit (−1 week) was 11.2/9.7% with a range of 9.9/8.5 to 14.0/12.3%. Details of the subjects participating in the study are summarised in Table 2.

No patient had any evidence of nephropathy or retinopathy at the initiation of the study.

TABLE 2

| PATIENT DETAILS | | | | |
|---|---|---|---|---|
| NUMBER | 1 | 2 | 3 | 4 |
| AGE (years) | 15 | 15 | 19 | 16 |
| SEX | M | M | M | M |
| PUBERTY STAGE (G/P.H.) | 5/5 | 3/2 | 5/5 | 5/5 |
| WT. (kg) | 61.0 | 78.0 | 38.5 | 83.8 | 28.7 |

Results

Metabolic control

Measured as $HbA_{1c(1)}$, which is a marker for metabolic control. The normal range for healthy is approximately 5–6% for $HbA_{1c}$.

Figure 6:
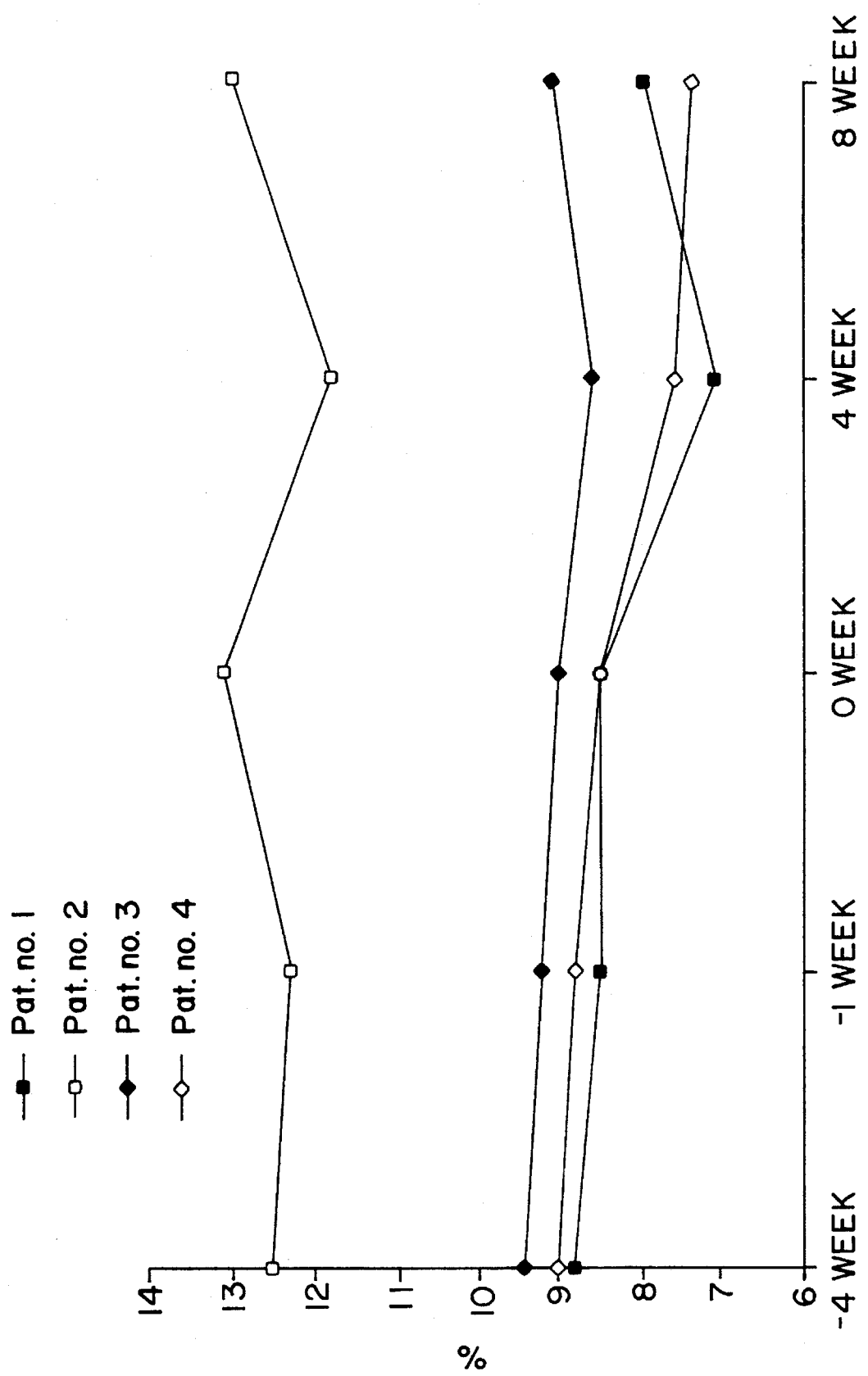
FIG. 6: IGF-I levels at −1, 0 and 4 week, respectively, for each patient, Example 2.

The individual data for the four patients are shown in FIG. 6.

Glycated haemoglobin levels, measured as $HbA_{1c(1)}$), tended to decrease during the 4 week treatment period and returned to a higher level after the IGF-I treatment (FIG. 6). Although one month observation period is too short to confirm a change in metabolic control (assessed by measurement of $HbA_{1c}$), a deterioration at discontinuation of IGF-I treatment implies that metabolic control can be affected by IGF-I. The observed changes lead further support to the invention that IGF-I treatment improves gylcaemic and metabolic control.

IGF-I

Table 3 shows the individual data for meanvalue over one night profile.

TABLE 3

| | IGF-I (U/ml) | | |
|---|---|---|---|
| | | Week | |
| PAT no | −1 | 0* | 4** |
| 1 | 1.34 | 2.04 | 2.48 |
| 2 | 0.90 | 1.51 | 2.02 |
| 3 | 1.13 | 1.82 | 2.48 |
| 4 | 1.37 | 2.07 | 2.16 |

*after first injection at 18.00 of IGF-I.
**after four weeks of daily injection of IGF-I.

During the 4 week treatment period IGF-I levels were maintained at normal physiological levels in healthy individuals of this age group.

Furthermore no suppression of endogenous IGF-I secretion was noted during the treatment period.

As a consequence, the long term normalisation of IGF-I levels would imply a normalisation of longitudinal growth in children and adolescence with IDDM.

We claim:

1. Method for treating Type 1 diabetes mellitus by subcutaneously administering to a patient suffering from Type 1 diabetes mellitus, IGF-1 in a dose effective to achieve an IGF-1 serum level of up to 400 ng/ml that is characteristic in healthy individuals.

2. The method of claim 1 wherein said patient suffering from Type I diabetes mellitus is a child, adolescent or young adult and said treating reduces the GH level.

3. The method of claim 2 wherein said treating reduces the insulin requirements of said patient.

4. The method of claim 1 wherein said treating is for improved and stabilized glycemic control in said patient as compared to not treating with said IGF-I.

5. The method of claim 1 wherein said patient suffering from Type I diabetes mellitus is a child or adolescent.

6. The method of claim 1 which comprises administering a medicament comprising said IGF-I and an insulin preparation.

7. The method of claim 1 which comprises administering a medicament containing said IGF-I by a single injection.

8. The method of claim 7 wherein a single injection is administered once or twice a day.

9. The method of claim 7 wherein a single injection is administered one to three times a week.

10. The method of claim 7 wherein a single injection is administered one to seven days a month.

11. The method of claim 7 wherein comprises administering a medicament containing said IGF-I in the form of a depot or slow release preparation.

12. The method of claim 1 wherein said IGF-I serum level characteristic in healthy individuals is about 200 ng/ml or about 400 ng/ml during puberty.

13. The method of claim 1 wherein said IGF-I is rh IGF-I.

* * * * *